United States Patent
Chang et al.

(10) Patent No.: US 11,103,181 B2
(45) Date of Patent: Aug. 31, 2021

(54) APPARATUS AND METHOD FOR PROCESSING BIO-INFORMATION

(71) Applicant: SAMSUNG ELECTRONICS CO., LTD., Suwon-si (KR)

(72) Inventors: Ki Young Chang, Yongin-si (KR); Jung Yong Nam, Hwaseong-si (KR); Kun Sun Eom, Yongin-si (KR); Joon Hyung Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 577 days.

(21) Appl. No.: 16/002,526

(22) Filed: Jun. 7, 2018

(65) Prior Publication Data
US 2019/0038218 A1    Feb. 7, 2019

(30) Foreign Application Priority Data
Aug. 1, 2017    (KR) .......................... 10-2017-0097749

(51) Int. Cl.
*A61B 5/00*    (2006.01)
*A61B 5/145*    (2006.01)
(Continued)

(52) U.S. Cl.
CPC .......... *A61B 5/4857* (2013.01); *A61B 5/1118* (2013.01); *A61B 5/1455* (2013.01);
(Continued)

(58) Field of Classification Search
CPC . A61B 5/4857; A61B 5/1118; A61B 5/14546; A61B 5/1455; A61B 5/4806;
(Continued)

(56) References Cited

U.S. PATENT DOCUMENTS

| | | | |
|---|---|---|---|
| 6,933,154 B2 | 8/2005 | Schomacker et al. | |
| 7,139,598 B2 | 11/2006 | Hull et al. | |

(Continued)

FOREIGN PATENT DOCUMENTS

| | | |
|---|---|---|
| CN | 106442417 A | 2/2017 |
| JP | 3747863 B2 | 2/2005 |

(Continued)

OTHER PUBLICATIONS

Statland, et al., "Factors Contributing to Intra-Individual Variation of Serum Constituents: 1. Within-Day Variation of Serum Constituents in Healthy Subjects", 1973, Clinical Chemistry, vol. 19, No. 12, pp. 1374-1379.

(Continued)

*Primary Examiner* — Catherine M Voorhees
*Assistant Examiner* — Roland Dinga
(74) *Attorney, Agent, or Firm* — Sughrue Mion, PLLC (57) ABSTRACT

A bio-information processing apparatus includes: an in vivo material measurer which measures an in vivo material of a user; and a processor which extracts a pattern of change of the in vivo material of the user based on a measurement result of the in vivo material, compares the extracted pattern of change of the in vivo material with a biological rhythm (Continued)

reference model, and determines whether biological rhythms of the user are disrupted based on a result of the comparison.

20 Claims, 7 Drawing Sheets (51) Int. Cl.
    *A61B 5/11*     (2006.01)
    *G06K 9/00*     (2006.01)
    *A61B 5/1455*     (2006.01)
    *G16H 50/20*     (2018.01)
    *G16H 50/70*     (2018.01)
    *G16H 50/30*     (2018.01)
    *G16H 10/40*     (2018.01)
    *A61B 5/01*     (2006.01)
    *A61B 5/024*     (2006.01)
    *A61B 5/021*     (2006.01)
    *A61B 5/0205*     (2006.01)

(52) U.S. Cl.
    CPC ........ *A61B 5/14546* (2013.01); *A61B 5/4806* (2013.01); *A61B 5/7246* (2013.01); *A61B 5/746* (2013.01); *G06K 9/00885* (2013.01); *G06K 9/00892* (2013.01); *G16H 10/40* (2018.01); *G16H 50/20* (2018.01); *G16H 50/30* (2018.01); *G16H 50/70* (2018.01); *A61B 5/01* (2013.01); *A61B 5/021* (2013.01); *A61B 5/024* (2013.01); *A61B 5/02055* (2013.01); *A61B 5/14532* (2013.01); *G06K 2009/00939* (2013.01)

(58) Field of Classification Search
    CPC ......... A61B 5/7246; A61B 5/746; A61B 5/01; A61B 5/02055; A61B 5/021; A61B 5/024; A61B 5/14532; G16H 10/40; G16H 50/30; G16H 50/70; G16H 50/20; G06K 9/00885; G06K 9/00892; G06K 2009/00939
See application file for complete search history.

(56) References Cited

U.S. PATENT DOCUMENTS

| | | | |
|---|---|---|---|
| 2005/0054907 A1* | 3/2005 | Page | A61B 5/0095 600/316 |
| 2005/0228295 A1 | 10/2005 | Tan | |
| 2008/0188763 A1* | 8/2008 | John | A61B 5/0452 600/516 |
| 2008/0269616 A1 | 10/2008 | Bloom et al. | |
| 2011/0144528 A1 | 6/2011 | Gurley | |
| 2012/0134985 A1 | 5/2012 | Evans et al. | |
| 2012/0242858 A1 | 9/2012 | Prigent et al. | |
| 2016/0120460 A1 | 5/2016 | Eom | |
| 2017/0007178 A1 | 1/2017 | Aubert et al. | |

FOREIGN PATENT DOCUMENTS

| | | |
|---|---|---|
| JP | 2017-18194 A | 1/2017 |
| KR | 10-2016-0052172 A | 5/2016 |
| WO | 03/079894 A1 | 10/2003 |

OTHER PUBLICATIONS

Pocock, et al., "Diurnal variations in serum biochemical and haematological measurements", 1989, Journal of Clinical Pathology, vol. 42, pp. 172-179.

Scheer, et al., "Adverse metabolic and cardiovascular consequences of circadian misalignment", Mar. 17, 2009, PNAS, vol. 106, No. 11, pp. 4453-4458.

Dallmann, et al., "The human circadian metabolome", Feb. 14, 2012, PNAS, vol. 109, No. 7, pp. 2625-2629.

Chua, et al., "Extensive diversity in circadian regulation of plasma lipids and evidence for different circadian metabolic phenotypes in humans", Aug. 27, 2013, PNAS, vol. 110, No. 35, pp. 14468-14473.

Adamovich, et al., "Circadian Clocks and Feeding Time Regulate the Oscillations and Levels of Hepatic Triglycerides", Feb. 4, 2014, Cell Metabolism, vol. 19, Issue 2, pp. 319-330.

Ancoli-Israel, et al., "The Role of Actigraphy in the Study of Sleep and Circadian Rhythms", 2003, American Academy of Sleep Medicine Review Paper, vol. 26, No. 3, pp. 342-392.

* cited by examiner

APPARATUS AND METHOD FOR PROCESSING BIO-INFORMATION

CROSS-REFERENCE TO RELATED APPLICATION

This application claims priority from Korean Patent Application No. 10-2017-0097749, filed on Aug. 1, 2017 in the Korean Intellectual Property Office, the disclosure of which is incorporated herein by reference in its entirety.

BACKGROUND

1. Field

Apparatuses and methods consistent with exemplary embodiments relate to processing bio-information of a subject.

2. Description of the Related Art

Biological rhythms are periodic physiological fluctuations in the human body, in which physiological activities, such as human brain waves, body temperature, blood pressure, heart rate, total body fluid and sodium, and the like, occur periodically according to ultradian rhythms having a predetermined period, circadian rhythms having about a 24-hour period, circatrigintan rhythms having about a one-month period, and circannual rhythms having about a one-year period.

As a standard method of measuring circadian rhythms, there is a method of measuring a change in the level of melatonin in saliva or blood, or a method of measuring bio-activity by using an accelerometer. However, such measuring methods have problems in that the methods are performed only in a limited measurement environment and under limited test conditions, such that it may be difficult to continuously monitor circadian rhythms easily in daily life; and the methods depend on only macroscopic movements, thus lowering accuracy and sensitivity of measurement.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided a bio-information processing apparatus including: an in vivo material measurer configured to measure an in vivo material of a user; and a processor configured to extract a pattern of change of the in vivo material of the user based on a measurement result of the in vivo material, and compare the extracted pattern of change of the in vivo material with a biological rhythm reference model, and determine whether biological rhythms of the user are disrupted based on a result of the comparison.

Here, the in vivo material may include at least one of triglyceride, free fatty acid, blood glucose, amino acid, and various hormone concentrations.

Further, the biological rhythms may include circadian rhythms.

The biological rhythm reference model may be classified into one or more groups based on user feature information which includes at least one of age, gender, stature, weight, and health information of a plurality of users, and based on user context information that includes at least one of sleep, meal, exercise, heart rate, blood pressure, body temperature, a measurement time, and a measurement place.

In addition, upon receiving a bio-information processing request from the user, the processor may select the biological rhythm reference model from among the one or more groups based on the user feature information and the user context information.

In this case, the pattern of change of the in vivo material may include at least one of an amount of change over time in the in vivo material, a time of reaching a maximum value of the in vivo material, and an area under curve (AUC) of a graph of a time-in vivo material concentration.

When at least one of a difference between the amount of change over time in the in vivo material and the amount of change in the biological rhythm reference model, a difference between the time of reaching the maximum value of the in vivo material and a time of reaching a maximum value in the biological rhythm reference model, and a difference between the area under curve (AUC) in the graph of the time-in vivo material concentration and an AUC in the biological rhythm reference model is outside a predetermined reference range, the processor determines that the biological rhythms of the user are disrupted.

Moreover, the in vivo material measurer may include: a light source configured to emit a light onto the user; and a detector configured to detect the light returning from the user.

Upon determining that the biological rhythms of the user are disrupted, the processor may generate warning information based on the determination.

The bio-information processing apparatus may further include an output interface configured to output at least one of the measured in vivo material information, the extracted pattern of change of the in vivo material, the determination on whether the biological rhythms are disrupted, and the warning information.

According to an aspect of another exemplary embodiment, there is provided a bio-information processing method including: measuring an in vivo material of a user; extracting a pattern of change of the in vivo material of the user based on a measurement result of the in vivo material; comparing the extracted pattern of change of the in vivo material with a biological rhythm reference model; and determining whether biological rhythms of the user are disrupted based on a result of the comparison.

Here, the in vivo material may include at least one of triglyceride, free fatty acid, blood glucose, amino acid, and various hormone concentrations.

Further, the biological rhythms may include circadian rhythms.

In addition, the biological rhythm reference model may be classified into one or more groups based on user feature information which includes at least one of age, gender, stature, weight, and health information of a plurality of users, and based on user context information that includes sleep, meal, exercise, heart rate, blood pressure, body temperature, a measurement time, and a measurement place.

The method may further include selecting the biological rhythm reference model from among the one or more groups based on the user feature information and the user context information in response to receiving a bio-information processing request.

Here, the pattern of change of the in vivo material may include at least one of an amount of change over time in the in vivo material, a time of reaching a maximum value of the in vivo material, and an area under curve (AUC) of a graph of a time-in vivo material concentration.

The determining whether the biological rhythms are disrupted may include determining that the biological rhythms of the user are disrupted in response to at least one of a difference between the amount of change over time in the in vivo material and an amount of change in the biological rhythm reference model, a difference between the time of reaching a maximum value of the in vivo material and a time of reaching a maximum value in the biological rhythm reference model, and a difference between the area under curve (AUC) in the graph of the time-in vivo material concentration and an AUC in the biological rhythm reference model being outside a predetermined reference range.

Here, the measuring of the in vivo material of the user may include: emitting a light onto the user; and detecting the light returning from the skin.

Further, upon determining that the biological rhythms of the user are disrupted, the bio-information processing method may include generating warning information based on the determination.

Moreover, the bio-information processing method may further include outputting at least one of the measured in vivo material information, the extracted pattern of change of the in vivo material, the determination on whether the biological rhythms are disrupted, and the warning information.

BRIEF DESCRIPTION OF THE DRAWINGS

The above and/or other aspects will be more apparent by describing certain exemplary embodiments, with reference to the accompanying drawings, in which.

DETAILED DESCRIPTION

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list.

Figure 1:
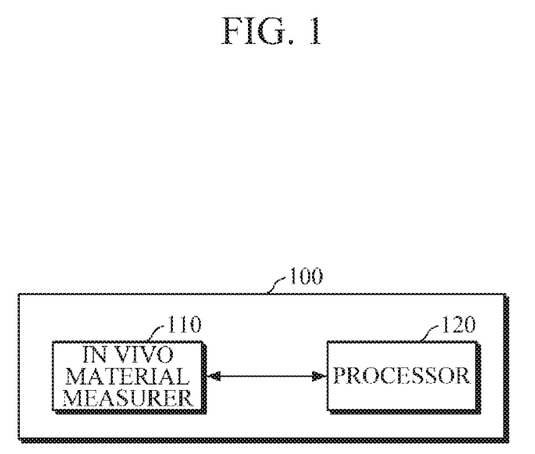
FIG. 1 illustrates a bio-information processing apparatus according to an exemplary embodiment.

FIG. 1 is a block diagram illustrating an example of a bio-information processing apparatus.

Referring to FIG. 1, the bio-information processing apparatus 100 may extract a pattern of change of an in vivo material of a user based on a measurement result of the in vivo material, may compare the extracted pattern of change of the in vivo material with a biological rhythm reference model to determine whether biological rhythms of the user are misaligned or disrupted, and may provide a determination result to the user.

Biological rhythms occur in the human body, and its periodicity may be broken or changed by external environment factors such as light, darkness, temperature, and life pattern. For example, working at night or irregular shifts may disrupt biological circadian rhythms and sleep/wake cycle. The disruption of biological circadian rhythms may cause psychosomatic disorders and impairment of performance efficiency. If biological rhythms occurring in the human body coincide with an external environment (e.g.: daytime/nighttime), it may be described that the biological rhythms are aligned, whereas if biological rhythms do not coincide with an external environment, it may be described that the biological rhythms are misaligned or disrupted. In other words, if the circadian clock of the body is synchronized with the cycles of nature (e.g., the sun, the moon, etc.), it may be described that the body is aligned with nature and the biological rhythms are aligned. Otherwise, the biological rhythms may be determined as being disrupted or misaligned.

Further, some of metabolites produced during in vivo metabolism after food intake correlate with a change in circadian rhythms, and the bio-information processing apparatus 100 may determine whether biological rhythms are misaligned or disrupted by monitoring and/or tracing a pattern of change of the in vivo material.

In this case, the in vivo material may include metabolites produced during metabolism, and may include at least one of triglyceride, free fatty acid, blood glucose, amino acid, and various hormone concentrations.

Hereinafter, for convenience of explanation, if necessary, description will be made based on an exemplary embodiment in which the bio-information processing apparatus 100 determines whether circadian rhythms are misaligned or disrupted by monitoring a pattern of change of blood triglyceride during lipid metabolism.

The bio-information processing apparatus 100 may be implemented as a software module or manufactured in the form of a hardware chip to be embedded in various types of electronic apparatuses. Examples of the electronic apparatuses may include a cellular phone, a smartphone, a tablet PC, a laptop computer, a personal digital assistant (PDA), a portable multimedia player (PMP), a navigation, an MP3 player, a digital camera, a wearable device, and the like, and examples of the wearable device may include a watch-type device, wristband-type device, a ring-type device, a waist belt-type device, a necklace-type device, an ankle band-type device, a thigh band-type device, a forearm band-type device, and the like. However, the electronic device is not limited to the above examples, and the wearable device is neither limited thereto.

Referring to FIG. 1, the bio-information processing apparatus 100 includes an in vivo material measurer 110 and a processor 120. Here, the processor 120 may be composed of one or more processors, a memory, and a combination thereof.

In the exemplary embodiment, the in vivo material measurer 110 may measure in vivo material by using a noninvasive method.

For example, the in vivo material measurer 110 may measure a change in the in vivo material at regular time intervals or successively, by emitting Near Infrared (NIR) light on a subject by using an optical method, and by detecting light returning therefrom. Further, the in vivo material measurer 110 may include one or more light sources and a detector, which will be described later in detail with reference to FIG. 3.

The processor 120 may extract a pattern of change of the in vivo material of a user based on a measurement result of the in vivo material.

In the exemplary embodiment, the processor 120 may monitor the in vivo material change over time based on information of the in vivo material change measured at regular time intervals or successively, and may extract the pattern of change of the in vivo material.

For example, based on the information of the in vivo material change measured at regular time intervals or successively, the processor 120 may produce a graph (graph of time-in vivo material concentration) of the in vivo material change over time, and may extract the pattern of change of the in vivo material from the graph of the time-in vivo material concentration.

Here, the pattern of change of the in vivo material may include at least one of the following: an amount of change over time in the in vivo material, a time of reaching a maximum value of the in vivo material, and an area under curve (AUC) of the graph of the time-in vivo material concentration. However, the pattern of change of the in vivo material is not limited thereto, and the processor 120 may extract, as the pattern of change of the in vivo material, a maximum value, a minimum value, an average value in the graph of the time-in vivo material concentration, a slope of a predetermined portion of the graph of the time-in vivo material concentration, and a shape of the graph of the time-in vivo material concentration.

Further, the processor 120 may determine whether biological rhythms of a user are misaligned or disrupted by comparing the extracted pattern of change of the in vivo material with the biological rhythm reference model.

Here, the biological rhythm reference model refers to aligned biological rhythms, and may be a target model to be used as a reference for comparison of the measured in vivo material change.

For example, the biological rhythm reference model may be generated or classified into one or more groups based on user feature information which includes one or more of age, gender, stature, weight, and health information; and based on user context information which includes sleep, meal, exercise, heart rate, blood pressure, body temperature, a measurement time, and a measurement place.

For example, based on user feature information indicative of 'a man in his thirties with a history of diabetes,' and user context information indicative of 'in sleep,' the biological rhythm reference model may be a biological rhythm reference model corresponding to 'thirties,' 'man,' 'history of diabetes,' and 'in sleep'. In this manner, the biological rhythm reference model may be classified into one or more groups or categories based on at least one of the user feature information and/or user context information. For example, the biological rhythm reference model may reflect biological rhythm characteristics of a group of "men in their thirties with a history of diabetes." In that case, the biological rhythm reference model may be generated based on human subjects that belong to the group of "men in their thirties with a history of diabetes" by monitoring the biological rhythms of the human subjects.

Upon receiving a bio-information processing request from a user, the processor 120 may select at least one biological rhythm reference model from among one or more of the groups or the categories based on the user feature information and the user context information.

For example, upon receiving a biological rhythm information processing request based on the measured in vivo material information, the processor 120 may compare the biological rhythm information with the measured in vivo material information based on the user feature information and the user context information, and may select an optimal biological rhythm reference model to determine whether biological rhythms are misaligned or disrupted. For example, in the case where the user feature information indicates a man in his thirties with a history of diabetes, the processor 120 selects a biological rhythm reference model, corresponding to 'thirties,' 'man,' and 'history of diabetes,' from the one or more biological rhythm reference model groups, and compares the selected biological rhythm reference model with the pattern of change of the measured in vivo material, to determine whether biological rhythms are misaligned or disrupted.

Among differences, including a difference between an amount of change over time in the in vivo material and an amount of change in the biological rhythm reference model, a difference between a time of reaching a maximum value of the in vivo material and a time of reaching a maximum value in the biological rhythm reference model, and a difference between the area under curve (AUC) in the graph of the time-in vivo material concentration and the AUC in the biological rhythm reference model, in the case where at least one of the differences falls outside of a predetermined reference range, the processor 120 may determine that a user's biological rhythms are misaligned or disrupted.

Hereinafter, with reference to FIGS. 2A and 2B, an example where the bio-information processing apparatus 100 determines whether a user's biological rhythms are misaligned or disrupted by comparing a pattern of change of an in vivo material with a biological rhythm reference model.

Figure 2A:
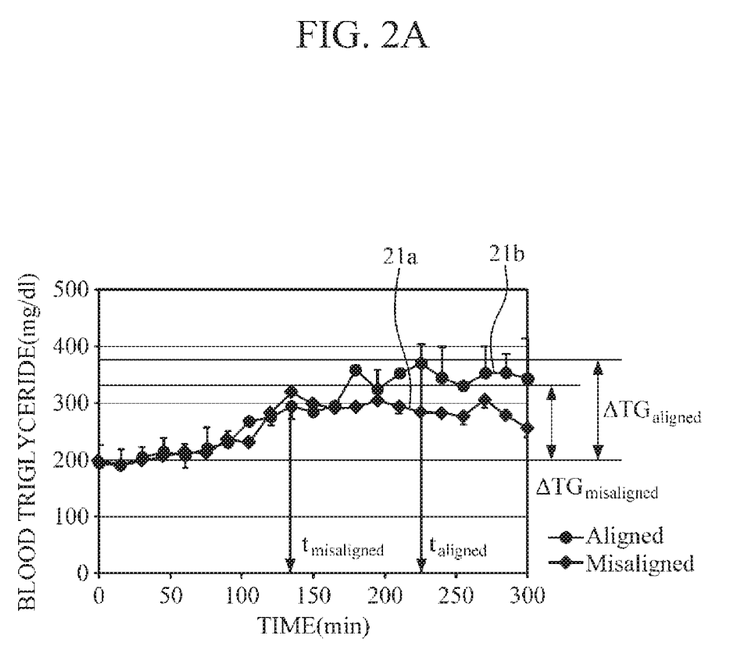
FIG. 2A is an exemplary diagram explaining an example of determining whether biological rhythms are misaligned or disrupted, by comparing a pattern of change of an in vivo material with a biological rhythm reference model.

FIG. 2A is an exemplary diagram explaining an example of determining whether biological rhythms are misaligned or disrupted, by comparing a pattern of change of an in vivo material with a biological rhythm reference model.

Referring to FIG. 2A, reference numeral 21a denotes a graph showing a change over time in blood triglyceride measured after food intake while biological rhythms are misaligned or disrupted; and reference numeral 21b denotes a graph showing a change over time in blood triglyceride of the biological rhythm reference model.

In the graph 21a showing a change over time in blood triglyceride measured after food intake while biological rhythms are misaligned or disrupted, a blood triglyceride concentration after food intake reaches a maximum value at time $t=t_{misaligned}$; and immediately after the food intake at $t=0$, and when the blood triglyceride reaches the maximum value at time $t=t_{misaligned}$, an amount of change $\Delta TG$ of the blood triglyceride concentration is represented as $\Delta TG_{misaligned}$.

Further, in the graph 21b showing a change over time in blood triglyceride of the biological rhythm reference model, a blood triglyceride concentration after food intake reaches a maximum value at time $t=t_{aligned}$; and during food intake at $t=0$, and when blood triglyceride reaches the maximum value at time $t=t_{aligned}$, an amount of change $\Delta TG$ of the blood triglyceride concentration is represented as $\Delta TG_{aligned}$. Here, the biological rhythm reference model may be a reference model selected by the processor 120 based on the user feature information and/or the user context information.

Referring to FIG. 2A, by comparing the amount of change over time $\Delta TG_{misaligned}$ in blood triglyceride measured after food intake while biological rhythms are misaligned or disrupted with the amount of change $\Delta TG_{aligned}$ of the blood triglyceride concentration of the biological rhythm reference model, it can be seen that the amount of change is relatively small. In this manner, when biological rhythms are misaligned or disrupted, an in vivo metabolism pattern is changed, causing a pattern of change of the in vivo material to be changed; and based on such pattern of change of the in vivo material and/or the in vivo material change by a metabolism pattern change, the processor 120 may determine whether biological rhythms are misaligned or disrupted.

In the exemplary embodiment, based on a difference between an amount of change over time $\Delta TG=\Delta TG_{subject}$ in blood triglyceride measured for a subject and an amount of change $\Delta TG_{aligned}$ of the blood triglyceride concentration of the biological rhythm reference model, the processor 120 may determine whether biological rhythms are misaligned or disrupted.

For example, the processor 120 monitors the change in the blood triglyceride concentration measured for a subject; calculates an amount of change $\Delta TG_{subject}$ of the blood triglyceride concentration during food intake at $t=0$ and when blood triglyceride reaches the maximum value at time $t=t_{aligned}$; compares the calculated amount of change $\Delta TG_{subject}$ of the blood triglyceride concentration of the subject with the amount of change $\Delta TG_{aligned}$ of the blood triglyceride concentration of the biological rhythm reference model; and in response to the calculated amount of change $\Delta TG_{subject}$ of the blood triglyceride concentration of the subject is smaller than the amount of change $\Delta TG_{aligned}$ of the blood triglyceride concentration of the biological rhythm reference model, the processor 120 may determine whether biological rhythms of the subject are misaligned or disrupted.

In another example, the processor 120 compares the calculated amount of change $\Delta TG_{subject}$ of the blood triglyceride concentration of the subject with the amount of change $\Delta TG_{aligned}$ of the blood triglyceride concentration of the biological rhythm reference model; and if a difference therebetween is at a level greater than or equal to a predetermined reference concentration (e.g.: 50 mg/dl), the processor 120 may determine that biological rhythms of the subject are misaligned or disrupted.

In yet another example, by comparing a time $t_{max}$ of reaching a maximum value of blood triglyceride measured for a subject with a time of reaching a maximum value of blood triglyceride of the biological rhythm reference model, the processor 120 may determine whether biological rhythms of a user are misaligned or disrupted.

Referring to FIG. 2A, in the graph 21a showing a change over time in blood triglyceride measured after food intake while biological rhythms are misaligned or disrupted, the blood triglyceride concentration after food intake reaches a maximum value at time $t=t_{misaligned}$; and in the graph 21b showing a change over time in blood triglyceride in the biological rhythm reference model, the blood triglyceride concentration after food intake reaches a maximum value at time $t=t_{aligned}$. In this manner, when biological rhythms are misaligned or disrupted, an in vivo metabolism pattern is changed, causing the pattern of change of the in vivo material to be changed; and based on such pattern of change of the in vivo material and/or the in vivo material change by a metabolism pattern change, the processor 120 may determine whether biological rhythms are misaligned or disrupted.

For example, the processor 120 monitors a change in the blood triglyceride concentration measured for a subject; determines or calculates a time $t=t_{subject}$ of reaching a maximum value of blood triglyceride after food intake; and in response to the time of reaching the maximum value thereof being ahead of the time of reaching the maximum value of the blood triglyceride concentration of the biological rhythm reference model, the processor 120 may determine that biological rhythms of the subject are misaligned or disrupted.

In another example, the processor 120 compares the calculated time $t=t_{subject}$ of reaching a maximum value of blood triglyceride of the subject with the time of reaching a maximum value of blood triglyceride in the biological rhythm reference model; and in response to a difference therebetween being a predetermined reference time (e.g.: 60 minutes) or more, the processor 120 may determine that biological rhythm of the subject are misaligned or disrupted.

However, the processor 120 is not limited thereto, and may determine whether biological rhythms of the subject are misaligned or disrupted by extracting, as a pattern of change of the blood triglyceride concentration measured for the subject, a maximum value, a minimum value, an average value of blood triglyceride, a slope of the graph of the blood triglyceride concentration change, and a shape of the graph of the blood triglyceride concentration change, and by comparing the pattern of change of the blood triglyceride concentration with the pattern of change of the blood triglyceride concentration in the biological rhythm reference model.

Figure 2B:
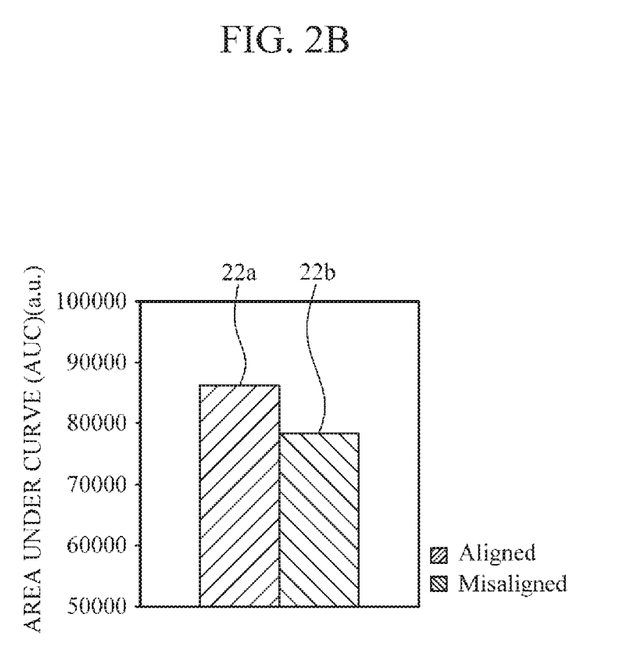
FIG. 2B is an exemplary diagram explaining another example of determining whether biological rhythms are misaligned or disrupted, by comparing a pattern of change of an in vivo material with a biological rhythm reference model.

FIG. 2B is an exemplary diagram explaining another example of determining whether biological rhythms are misaligned or disrupted, by comparing a pattern of change of an in vivo material with a biological rhythm reference model.

In the embodiment, the processor 120 may determine whether biological rhythms of a user are misaligned or disrupted based on the area under curve (AUC) of the graph of the time-in vivo material concentration and the AUC of the biological rhythm reference model.

Referring to FIGS. 1, 2A, and 2B, the processor 120 may calculate the AUCs 22a and 22b on the graph 21a showing a change over time in blood triglyceride measured after food intake while biological rhythms are misaligned or disrupted, and on the graph 21b showing a change over time in blood triglyceride of the biological rhythm reference model.

For example, the processor 120 monitors the change of the blood triglyceride concentration measured for the subject, and calculates the AUC on the graph showing the change over time in blood triglyceride measured after food intake. In response to the calculated AUC being smaller than the AUC calculated from the graph 22a showing the change over time in blood triglyceride of the biological rhythm reference model, the processor 120 may determine that biological rhythms of the subject are misaligned or disrupted.

In another example, the processor 120 compares the AUC calculated from the graph showing the change in the blood triglyceride of the subject with the AUC calculated from the graph 22a showing the change over time in blood triglyceride of the biological rhythm reference model; and in response to a difference between the AUCs being greater than or equal to a predetermined reference value (e.g.; difference greater than or equal to 15%), the processor 120 may determine that biological rhythms of the subject are misaligned or disrupted.

Upon determining that biological rhythms of a user are misaligned or disrupted, the processor 120 may generate warning information based on the determination. In the exemplary embodiment, once the processor 120 determines that the user's biological rhythms are misaligned or disrupted in response to a request for determination whether the user's biological rhythms are aligned or misaligned, or based on a monitoring result of the pattern of change of the in vivo material, the processor 120 may generate warning information to inform the user of the determination. Here, warning information may include information on whether biological rhythms are misaligned or disrupted, multiple-stage alarm according to a degree of misalignment, or information on measures in response to determination of misalignment of biological rhythms.

Figure 3:
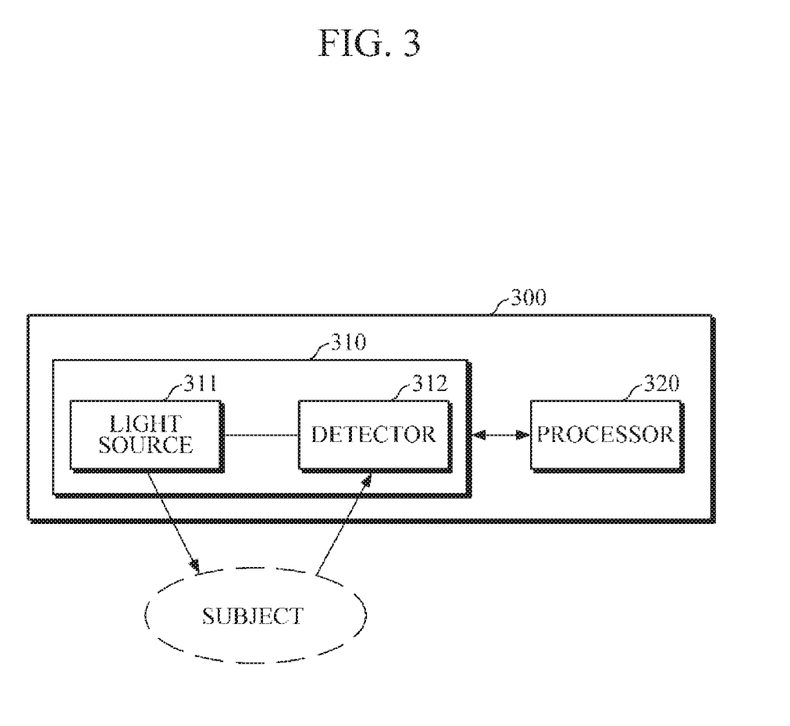
FIG. 3 illustrates a bio-information processing apparatus according to another exemplary embodiment.

FIG. 3 is a block diagram illustrating another example of a bio-information processing apparatus.

Referring to FIG. 3, a bio-information processing apparatus 300 includes an in vivo material measurer 310 and a processor 320. Here, the processor 320 may perform substantially the same function as the processor 120 illustrated in FIG. 1, such that description below will be made based on details that do not overlap.

The in vivo material measurer 310 may include one or more light sources 311 and a detector 312. The in vivo material measurer 310 may measure the in vivo material successively or at predetermined time intervals by using a noninvasive method, and may obtain successive data to determine whether a user's biological rhythms are misaligned or disrupted.

In the exemplary embodiment, the light source 311 may emit light on a subject. For example, the light source 311 may emit light of a specific wavelength, e.g., near infrared (NIR), on the subject. However, the wavelength of light emitted by the light source 311 may vary depending on the purpose of measurement or types of components to be measured. Further, the light source 311 is not necessarily required to be configured as a single light emitting body, but may be configured as a group of a plurality of light emitting bodies. In the case where the light source 311 is configured as a group of a plurality of light emitting bodies, the light emitting bodies may emit light of different wavelengths to serve the purpose of measurement, or may emit light of the same wavelength. In the exemplary embodiment, the light source 311 may include a light emitting diode (LED), a laser diode, or the like, but this is only exemplary, and the light source 311 is not limited thereto.

The detector 312 may include a plurality of light detectors. Each light detector 312 may detect light reflected or scattered from an object to be inspected (e.g., skin, etc.), and may measure the intensity of the detected light. In the exemplary embodiment, the detector 312 may include a photo diode, a photo transistor (PTr), a charge-coupled device (CCD), or the like.

The processor 320 may control the optical wavelength and intensity of the light source 311 according to the purpose of measurement or types of components to be measured. In the case where the light sources are configured as a group of a plurality of light emitting bodies, the processor 320 may select one or more light sources or may control light emission to serve the purpose of measurement.

The processor 320 monitors an in vivo material change by analyzing the intensity of light detected by the detector 312 for each wavelength region range, thereby successively monitoring the in vivo material change by using a noninvasive method.

Figure 4:
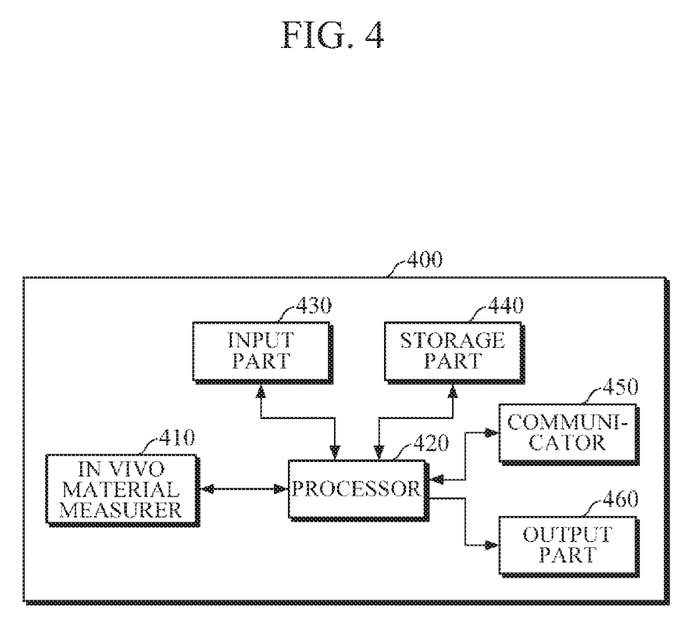
FIG. 4 illustrates a bio-information processing apparatus according to another exemplary embodiment.

FIG. 4 is a block diagram illustrating yet another example of a bio-information processing apparatus.

Referring to FIG. 4, the bio-information processing apparatus 400 includes an in vivo material measurer 410, a processor 420, an input part (e.g., an input interface) 430, a storage part 440, a communicator 450, and an output part (e.g., an output interface) 460. Here, the in vivo material measurer 410 and the processor 420 perform the same functions as the in vivo material measurers 110 and 310 and the processors 120 and 320 which are described above with reference to FIGS. 1 and 3, such that description below will be made based on details that do not overlap.

The input part 430 may receive various operation signals and data required for processing bio-information from a user. In the embodiment, the input unit 430 may include a keypad, a dome switch, a touch pad (static pressure/static electricity), a jog wheel, a jog switch, a hardware (H/W) button, and the like. Particularly, the touch pad, which forms a layer structure with a display, may be called a touch screen.

For example, the input part 430 may receive user feature information which includes one or more of age, gender, stature, weight, and health information; and user context information which includes sleep, meal, exercise, heart rate, blood pressure, body temperature, a measurement time and a measurement place.

For example, a user may input information on ingested food and current activities through the input part 430. The processor 420 may select a biological rhythm reference model based on the input information, thereby determining misalignment of biological rhythms more accurately.

The storage part 440 may store programs or commands for operation of the bio-information processing apparatus 400, and may store data input to and output from the bio-information processing apparatus 400. For example, the storage part 440 may store the user feature information and user context information which are input through the input part 430, the in vivo material information which is measured by the in vivo material measurer 410, the biological rhythm reference model and one or more groups thereof, the pattern of change of the in vivo material which is calculated by the processor 420, and the like.

The storage part 440 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the bio-information processing apparatus

400 may operate an external storage medium, such as web storage and the like, which performs a storage function of the storage part 440 on the Internet.

The communicator 450 may perform communication with an external device. For example, the communicator 450 may transmit, to the external device, the user feature information and user context information which are input by a user through the input part 430, the in vivo material information which is measured by the in vivo material measurer 410, a result of determination on misalignment of biological rhythms by the processor 530, and the like, or may receive various data, from the external device, the measured in vivo material information of a user, the biological rhythm reference model, and the like, which may be useful to determine whether biological rhythms are misaligned or disrupted.

In this case, the external device may be a database (DB) which stores the biological rhythm reference model, and/or a medical device which uses a determination result of misalignment of biological rhythms, a printer to output results, or a display device which displays a determination result of misalignment of biological rhythms. In addition to these devices, examples of the external device may include a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 450 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, ultra-wideband (UWB) communication, Ant+ communication, WIFI communication, Radio Frequency Identification (RFID) communication, 3G communication, 4G communication, 5G communication, and the like. However, this is merely exemplary and the communicator is not limited thereto.

The output part 460 may output, by the control of the processor 420, one or more of the measured in vivo material information, the extracted pattern of change of the in vivo material, a result of determination on whether biological rhythms are misaligned or disrupted, and warning information. In the embodiment, the output part 460 may output one or more of the measured in vivo material information, the extracted pattern of change of the in vivo material, a result of determination on whether biological rhythms are misaligned or disrupted, and warning information, by using at least one of an acoustic method, a visual method, and a tactile method. To this end, the output part 460 may include a display, a speaker, a vibrator, and the like.

Figure 5:
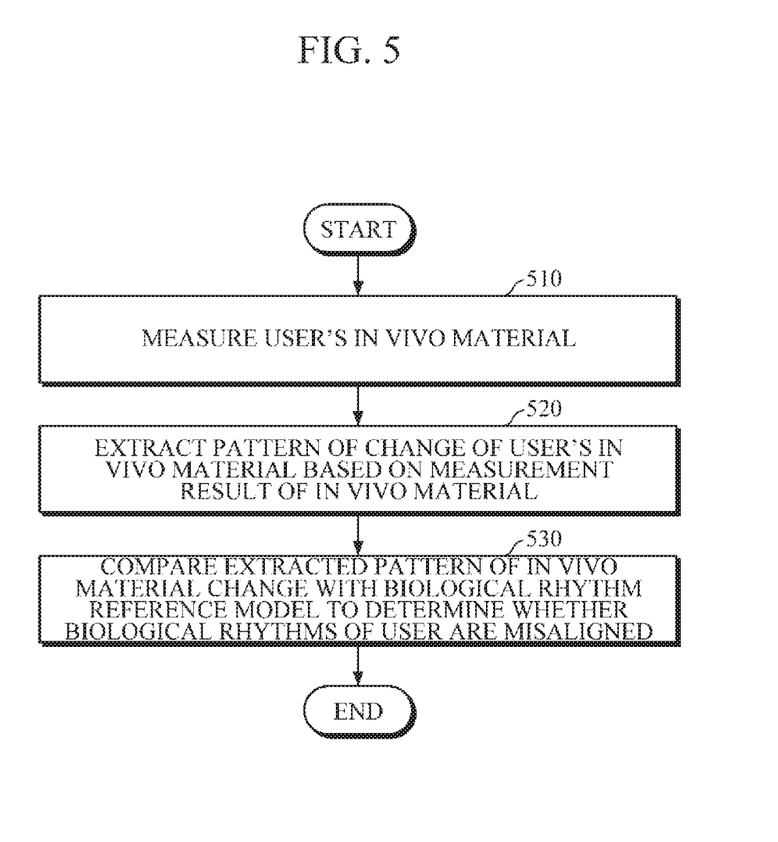
FIG. 5 illustrates a bio-information processing method according to an exemplary embodiment.

FIG. 5 is a flowchart illustrating an example of a bio-information processing method. The bio-information processing method illustrated in FIG. 5 may be performed by the bio-information processing apparatus 100 illustrated in FIG. 1.

The bio-information processing apparatus 100 may measure a user's in vivo material in operation 510.

In the exemplary embodiment, the bio-information processing apparatus 100 may measure the in vivo material by using a noninvasive method. For example, the bio-information processing apparatus 100 may measure the in vivo material change at regular time intervals or successively by emitting Near Infrared (NIR) light on a subject by using an optical method, and by detecting light returning therefrom. Based on the measurement, the bio-information processing apparatus 100 may obtain successive data to determine whether biological rhythms are misaligned or disrupted.

Upon measuring the in vivo material, the bio-information processing apparatus 100 may extract a pattern of change of the user's in vivo material based on a measurement result of the in vivo material in operation 520.

In the exemplary embodiment, based on the in vivo material change information measured at regular time intervals or successively, the bio-information processing apparatus 100 may monitor the in vivo material change over time, and may extract the pattern of change of the in vivo material.

For example, based on the in vivo material change information measured at regular time intervals or successively, the bio-information processing apparatus 100 may produce a graph (graph of time-in vivo material concentration) of the in vivo material change over time, and may extract the pattern of the in vivo material change from the graph of the time-in vivo material concentration. Here, the pattern of the in vivo material change may include at least one of the following: the in vivo material change over time, a time of reaching a maximum value of the in vivo material, and an area under curve (AUC) of the graph of the time-in vivo material concentration. However, the pattern of the in vivo material change is not limited thereto, and the bio-information processing apparatus 100 may extract, as the pattern of the in vivo material change, a maximum value, a minimum value, an average value in the graph of the time-in vivo material concentration, an slope of a predetermined portion of the graph of the time-in vivo material concentration, and a shape of the graph of the time-in vivo material concentration.

Upon extracting the pattern of the in vivo material change, the bio-information processing apparatus 100 compares the extracted pattern of change of the in vivo material with the biological rhythm reference model, to determine whether biological rhythms of the user are misaligned or disrupted in operation 530.

For example, among differences, including a difference between an amount of change over time in the in vivo material and an amount of change in the biological rhythm reference model, a difference between a time of reaching a maximum value of the in vivo material and a time of reaching a maximum value in the biological rhythm reference model, and a difference between the area under curve (AUC) in the graph of the time-in vivo material concentration and the AUC in the biological rhythm reference model, in the case where at least one of the differences falls outside of a predetermined reference range, the bio-information processing apparatus 100 may determine that the biological rhythms of the user are misaligned or disrupted.

In the exemplary embodiment, when biological rhythms are misaligned or disrupted, an in vivo metabolism pattern is changed, causing a pattern of change of the in vivo material to be changed; and based on such pattern of change of the in vivo material and/or the in vivo material change by a metabolism pattern change, the bio-information processing apparatus 100 may determine whether biological rhythms are misaligned or disrupted.

For example, the bio-information processing apparatus 100 monitors a change in the blood triglyceride concentration measured for a subject; calculates an amount of change of the blood triglyceride concentration immediately after food intake and when blood triglyceride reaches the maximum value; compares the calculated amount of change of the blood triglyceride concentration of the subject with the amount of change of the blood triglyceride concentration of the biological rhythm reference model; and in response to the calculated amount of change of the blood triglyceride concentration of the subject being smaller than the amount of change of the blood triglyceride concentration of the biological rhythm reference model, the bio-information processing apparatus 100 may determine that biological rhythms of the subject are misaligned or disrupted.

In another example, the bio-information processing apparatus 100 compares the calculated amount of change of the blood triglyceride concentration of the subject with the amount of change of the blood triglyceride concentration of the biological rhythm reference model; and in response to a difference therebetween being greater than or equal to a predetermined reference concentration (e.g.: 50 mg/dl), the bio-information processing apparatus 100 may determine that biological rhythms of the subject are misaligned or disrupted.

In yet another example, by comparing a time of reaching a maximum value of the blood triglyceride measured for a subject with a time of reaching a maximum value of the blood triglyceride of the biological rhythm reference model, the bio-information processing apparatus 100 may determine whether a user's biological rhythms are misaligned or disrupted.

For example, the bio-information processing apparatus 100 monitors the change in the blood triglyceride concentration measured for a subject; calculates a time of reaching a maximum value of the blood triglyceride after food intake; and in response to the calculated time of reaching the maximum value thereof being ahead of the time of reaching the maximum value of the blood triglyceride concentration of the biological rhythm reference model, the bio-information processing apparatus 100 may determine that biological rhythms of the subject are misaligned or disrupted.

In another example, the bio-information processing apparatus 100 compares the calculated time of reaching the maximum value of the blood triglyceride of the subject with the time of reaching the maximum value of the blood triglyceride of the biological rhythm reference model; and in response to a difference therebetween being a predetermined reference time (e.g.: 60 minutes) or more, the bio-information processing apparatus 100 may determine that biological rhythms are misaligned or disrupted.

In yet another example, based on a difference between the area under curve (AUC) of the graph of the time-in vivo material concentration and the AUC of the biological rhythm reference model, the bio-information processing apparatus 100 may determine whether biological rhythms of a user are misaligned or disrupted.

The bio-information processing apparatus 100 may calculate AUCs 21b and 22b on the graph 21a showing a change over time in blood triglyceride measured after food intake while biological rhythms are misaligned or disrupted, and on the graph 22a showing a change over time in blood triglyceride of the biological rhythm reference model.

For example, the bio-information processing apparatus 100 monitors the change of the blood triglyceride concentration measured for the subject; calculates the AUC from the graph showing the change over time in blood triglyceride measured after food intake; and in response to the calculated AUC being smaller than the AUC calculated from the graph showing the change over time in blood triglyceride of the biological rhythm reference model, the bio-information processing apparatus 100 may determine that biological rhythms of the subject are misaligned or disrupted.

In another example, the bio-information processing apparatus 100 compares the AUC calculated from the graph showing the change in the blood triglyceride of the subject with the AUC calculated from the graph 22a showing the change over time in blood triglyceride of the biological rhythm reference model; and in response to a difference between the AUCs being greater than or equal to a predetermined reference value (e.g.; difference greater than or equal to 15%), the bio-information processing apparatus 100 may determine that biological rhythms of the subject are misaligned or disrupted.

However, the bio-information processing apparatus 100 is not limited thereto, and may determine whether biological rhythms of the subject are misaligned or disrupted by extracting, as a pattern of change of the blood triglyceride concentration measured for the subject, a maximum value, a minimum value, an average value of blood triglyceride, a slope of the graph of the blood triglyceride concentration change, and a shape of the graph of the blood triglyceride concentration change, and by comparing the pattern of change of the blood triglyceride concentration with the pattern of change of the blood triglyceride concentration in the biological rhythm reference model.

Figure 6:
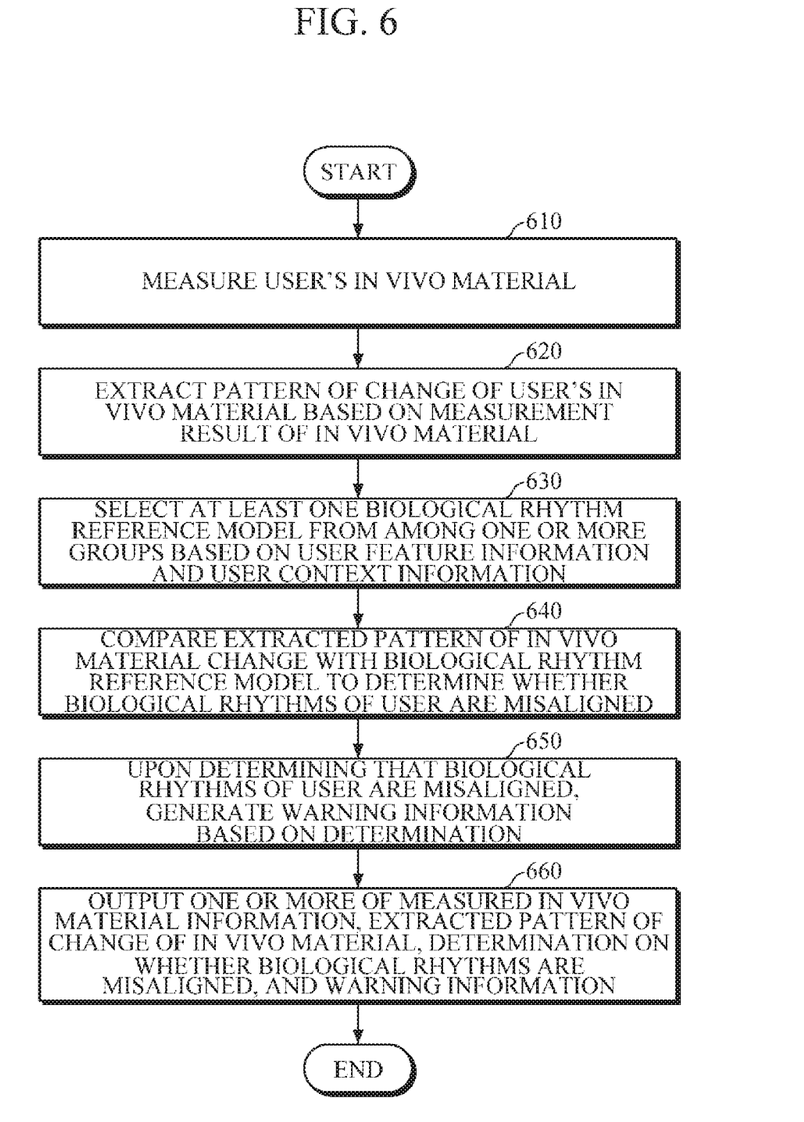
FIG. 6 illustrates a bio-information processing method according to another exemplary embodiment.

FIG. 6 is a flowchart illustrating an example of a bio-information processing method. The bio-information processing method of FIG. 6 may be performed by the bio-information processing apparatuses 100, 300, and 400 of FIG. 1, 3, or 4.

The bio-information processing apparatus 400 may measure a user's in vivo material in operation 610. For example, the bio-information processing apparatus 400 may measure the in vivo material by emitting Near Infrared (NIR) light on the skin, and by detecting light returning by being scattered from the skin.

Upon measuring the in vivo material, the bio-information processing apparatus 400 may extract a pattern of a user's in vivo material change based on a measurement result of the in vivo material in operation 620.

Upon receiving a bio-information processing request from a user, the bio-information processing apparatus 400 may select at least one biological rhythm reference model from among one or more groups based on the user feature information and the user context information in operation 630.

Here, the biological rhythm reference model may be generated into one or more groups based on user feature information which includes one or more of age, gender, stature, weight, and health information; and based on user context information which includes sleep, meal, exercise, heart rate, blood pressure, body temperature, a measurement time, and a measurement place.

For example, based on user feature information indicative of 'a man in his thirties with a history of diabetes,' and user context information indicative of 'in sleep,' the biological rhythm reference model may be a biological rhythm reference model corresponding to 'thirties,' 'man,' 'history of diabetes,' and 'in sleep'. In this manner, the biological rhythm reference model may be generated into groups based on at least one of the user feature information and/or user context information.

In the embodiment, upon receiving a bio-information processing request from a user, the bio-information processing apparatus 400 may select at least one biological rhythm reference model from among one or more groups based on the user feature information and the user context information For example, upon receiving a bio-information processing request based on the measured in vivo material information, the bio-information processing apparatus 400 may compare the bio-information with the measured in vivo material information based on the user feature information and the user context information, and may select an optimal biological rhythm reference model to determine whether biological rhythms are misaligned or disrupted. For example, in the case where the user feature information indicates a man in his thirties with a history of diabetes, the bio-information processing apparatus 400 selects a biological rhythm reference model, corresponding to 'thirties,' 'man,' and 'history of diabetes,' from the one or more biological rhythm reference model groups.

Upon extracting the pattern of the in vivo material change, the bio-information processing apparatus 400 may compare the extracted pattern of change of the in vivo material with the biological rhythm reference model, may determine whether biological rhythms are misaligned or disrupted in operation 640.

For example, upon extracting the pattern of the in vivo material change, the bio-information processing apparatus 400 may compare the extracted pattern of the in vivo material change with the biological rhythm reference model selected based on at least one of the user feature information and/or the user context information, and may determine whether biological rhythms are misaligned or disrupted.

For example, among differences, including a difference between an amount of change over time in the in vivo material and an amount of change in the biological rhythm reference model, a difference between a time of reaching a maximum value of the in vivo material and a time of reaching a maximum value in the biological rhythm reference model, and a difference between the area under curve (AUC) in the graph of the time-in vivo material concentration and the AUC in the biological rhythm reference model, in the case where at least one of the differences falls outside of a predetermined reference range, the bio-information processing apparatus 400 may determine that the biological rhythms of the user are misaligned or disrupted.

Upon determining that the biological rhythms of the user are misaligned or disrupted, the bio-information processing apparatus 400 may generate warning information based on the determination in operation 650.

In the embodiment, once the bio-information processing apparatus 400 determines that the user's biological rhythms are misaligned or disrupted in response to a request for determination whether the user's biological rhythms are aligned or misaligned, or based on a monitoring result of the pattern of change of the in vivo material, the bio-information processing apparatus 400 may generate warning information to inform the user of the determination. Here, warning information may include information on whether biological rhythms are misaligned or disrupted, multiple-stage alarm according to a degree of misalignment, or information on measures in response to determination of misalignment of biological rhythms.

The bio-information processing apparatus 400 may output one or more of the measured in vivo material information, the extracted pattern of the in vivo material change, a result of determination on whether biological rhythms are misaligned or disrupted, and warning information in operation 660. For example, the bio-information processing apparatus 400 may output one or more of the measured in vivo material information, the extracted pattern of the in vivo material change, a result of determination on whether the biological rhythms are misaligned or disrupted, and warning information.

In the exemplary embodiment, the bio-information processing apparatus 400 may output one or more of the measured in vivo material information, the extracted pattern of the in vivo material change, a result of determination on whether biological rhythms are misaligned or disrupted, and warning information, by using at least one of an acoustic method, a visual method, and a tactile method.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A bio-information processing apparatus, comprising:
an in vivo material measurer configured to measure an in vivo material of a user; and
a processor configured to extract a pattern of change of the in vivo material of the user based on information of the change of the in vivo material that is measured at regular time intervals or successively, and compare the extracted pattern of change of the in vivo material with a biological rhythm reference model, and determine whether biological rhythms of the user are disrupted based on a result of the comparison.

2. The apparatus of claim 1, wherein the in vivo material comprises at least one of triglyceride, free fatty acid, blood glucose, amino acid, and various hormone concentrations.

3. The apparatus of claim 1, wherein the biological rhythms are circadian rhythms.

4. The apparatus of claim 1, wherein the biological rhythm reference model is classified into one or more groups based on user feature information that comprises at least one of age, gender, stature, weight, and health information of a plurality of users, and based on user context information that comprises at least one of sleep, meal, exercise, heart rate, blood pressure, body temperature, a measurement time, and a measurement place.

5. The apparatus of claim 4, wherein upon receiving a bio-information processing request from the user, the processor selects the biological rhythm reference model from among the one or more groups based on the user feature information and the user context information.

6. The apparatus of claim 1, wherein the pattern of change of the in vivo material comprises at least one of an amount of change over time in the in vivo material, a time of reaching a maximum value of the in vivo material, and an area under curve (AUC) of a graph of a time-in vivo material concentration.

7. The apparatus of claim 6, wherein in response to at least one of a difference between the amount of change over time in the in vivo material and an amount of change in the biological rhythm reference model, a difference between the time of reaching the maximum value of the in vivo material and a time of reaching a maximum value in the biological rhythm reference model, and a difference between the area under curve (AUC) in the graph of the time-in vivo material concentration and an AUC in the biological rhythm reference model being outside a predetermined reference range, the processor determines that the biological rhythms of the user are disrupted.

8. The apparatus of claim 1, wherein the in vivo material measurer comprises:
a light source configured to emit a light onto the user; and
a detector configured to detect the light returning from the user.

9. The apparatus of claim 1, wherein upon determining that the biological rhythms of the user are disrupted, the processor generates warning information based on the determination.

10. The apparatus of claim 9, further comprising an output interface configured to output at least one of the measured in vivo material information, the extracted pattern of change of the in vivo material, the determination on whether the biological rhythms are disrupted, and the warning information.

11. A bio-information processing method, comprising:
measuring an in vivo material of a user;
extracting a pattern of change of the in vivo material of the user based on information of the change of the in vivo material that is measured at regular time intervals or successively;
comparing the extracted pattern of change of the in vivo material with a biological rhythm reference model; and
determining whether biological rhythms of the user are disrupted based on a result of the comparison.

12. The method of claim 11, wherein the in vivo material comprises at least one of triglyceride, free fatty acid, blood glucose, amino acid, and various hormone concentrations.

13. The method of claim 11, wherein the biological rhythms are circadian rhythms.

14. The method of claim 11, wherein the biological rhythm reference model is classified into one or more groups based on user feature information that comprises at least one of age, gender, stature, weight, and health information of a plurality of users, and based on user context information that comprises sleep, meal, exercise, heart rate, blood pressure, body temperature, a measurement time, and a measurement place.

15. The method of claim 14, further comprising selecting the biological rhythm reference model from among the one or more groups based on the user feature information and the user context information in response to receiving a bio-information processing request.

16. The method of claim 11, wherein the pattern of change of the in vivo material comprises at least one of an amount of change over time in the in vivo material, a time of reaching a maximum value of the in vivo material, and an area under curve (AUC) of a graph of a time-in vivo material concentration.

17. The method of claim 16, wherein the determining whether the biological rhythms are disrupted comprises determining that the biological rhythms of the user are disrupted in response to at least one of a difference between the amount of change over time in the in vivo material and an amount of change in the biological rhythm reference model, a difference between the time of reaching a maximum value of the in vivo material and a time of reaching a maximum value in the biological rhythm reference model, and a difference between the area under curve (AUC) in the graph of the time-in vivo material concentration and an AUC in the biological rhythm reference model being outside a predetermined reference range.

18. The method of claim 11, wherein the measuring of the in vivo material of the user comprises:
emitting a light onto the user; and
detecting the light returning from the user.

19. The method of claim 11, comprising, upon determining that the biological rhythms of the user are disrupted, generating warning information based on the determination.

20. The method of claim 19, further comprising outputting at least one of the measured in vivo material information, the extracted pattern of change of the in vivo material, the determination on whether the biological rhythms are disrupted, and the warning information.

* * * * *